United States Patent
Ben

(10) Patent No.: US 11,052,108 B2
(45) Date of Patent: Jul. 6, 2021

(54) AMORPHOUS CALCIUM CARBONATE FOR TREATING A LEUKEMIA

(71) Applicant: AMORPHICAL LTD., Ness Ziona (IL)

(72) Inventor: Yosef Ben, Arava (IL)

(73) Assignee: AMORPHICAL LTD., Ness Ziona (IL)

( * ) Notice: Subject to any disclaimer, the term of this patent is extended or adjusted under 35 U.S.C. 154(b) by 0 days.

(21) Appl. No.: 16/343,463

(22) PCT Filed: Oct. 23, 2017

(86) PCT No.: PCT/IL2017/051160
§ 371 (c)(1),
(2) Date: Apr. 19, 2019

(87) PCT Pub. No.: WO2018/078616
PCT Pub. Date: May 3, 2018

(65) Prior Publication Data
US 2019/0262391 A1      Aug. 29, 2019

Related U.S. Application Data

(60) Provisional application No. 62/412,300, filed on Oct. 25, 2016.

(51) Int. Cl.
| A61K 33/10 | (2006.01) |
| A23L 29/00 | (2016.01) |
| A61P 35/02 | (2006.01) |
| A61K 9/00 | (2006.01) |
| A61K 31/66 | (2006.01) |

(52) U.S. Cl.
CPC ............ *A61K 33/10* (2013.01); *A23L 29/015* (2016.08); *A61K 9/0053* (2013.01); *A61K 31/66* (2013.01); *A61P 35/02* (2018.01)

(58) Field of Classification Search
CPC ........ A61K 33/10; A23L 29/015; A61P 35/02
See application file for complete search history.

(56) References Cited

U.S. PATENT DOCUMENTS

| 4,199,496 | A | 4/1980 | Johnson |
| 4,237,147 | A | 12/1980 | Merten |
| 4,964,894 | A | 10/1990 | Freepons |
| 5,437,857 | A | 8/1995 | Tung |
| 5,886,012 | A | 3/1999 | Pang |
| 6,265,200 | B1 | 7/2001 | De Leys |
| 6,348,571 | B1 | 2/2002 | Redei |
| 6,569,472 | B1 | 5/2003 | Zyck |
| 8,324,301 | B2 | 12/2012 | Cavalier |
| 8,728,533 | B2 | 5/2014 | Ben |
| 8,802,160 | B2 | 8/2014 | Bentov |
| 9,149,494 | B2 | 10/2015 | Sagi |
| 9,550,878 | B2 | 1/2017 | Meiron |
| 2003/0077604 | A1 | 4/2003 | Sun |
| 2004/0028748 | A1 | 2/2004 | Sasaya |
| 2004/0234614 | A1 | 11/2004 | Strong |
| 2006/0165784 | A1 | 7/2006 | Zhao |
| 2007/0041506 | A1 | 2/2007 | Bottino |
| 2007/0191963 | A1 | 8/2007 | Winterbottom |
| 2008/0095819 | A1 | 4/2008 | Gourdie |
| 2010/0096330 | A1 | 4/2010 | Gotch |
| 2011/0313052 | A1 | 12/2011 | Engqvist |
| 2013/0122117 | A1* | 5/2013 | Ben .................. A61P 19/00 424/687 |
| 2013/0190441 | A1 | 7/2013 | Vucak |
| 2015/0056306 | A1* | 2/2015 | Sagi ................... A61K 33/10 424/687 |

FOREIGN PATENT DOCUMENTS

| CA | 2806131 A1 | 2/2012 |
| CN | 101314031 A | 12/2008 |
| CN | 101580260 A | 11/2009 |
| CN | 101969962 A | 2/2011 |
| CN | 102085356 A | 6/2011 |
| CN | 103663532 B | 10/2015 |
| EP | 0052677 A1 | 6/1982 |
| EP | 1666046 A1 | 6/2006 |
| GB | 2217988 A | 11/1989 |
| JP | H01156985 A | 6/1989 |
| JP | H099871 A | 1/1997 |
| JP | H10236957 A | 9/1998 |
| JP | 2002504140 A | 2/2002 |
| JP | 2003292453 A | 10/2003 |
| JP | 2004081739 A | 3/2004 |
| JP | 2008500332 A | 1/2008 |
| JP | 2008545845 A | 12/2008 |
| JP | 2011501676 A | 1/2011 |
| KR | 1020020082813 A | 10/2002 |

(Continued)

OTHER PUBLICATIONS

Bolouri et al (Nature Medicine, 2018, vol. 24, pp. 103-112) (Year: 2018).*
Garcia-Escobar et al (Critical Reviews in Oncology/Hematology, 2011, vol. 80, pp. 100-113) (Year: 2011).*
Tsimberidou et al (Blood, 2005, vol. 106, p. 921) (Year: 2005).*
Saitoh et al., (1985) Inhibition of calcium-carbonate precipitation by human salivary proline-rich phosphoproteins. Arch Oral Biol 30(8): 641-643.
Sawada (1997) The mechanisms of crystallization and transformation of calcium carbonates. Pure and Applied Chemistry 69(5): 921-928.

(Continued)

*Primary Examiner* — Mark V Stevens
(74) *Attorney, Agent, or Firm* — Dorsey & Whitney LLP

(57) ABSTRACT

The present invention provides compositions and methods of treating a leukemia, including chronic lymphocytic leukemia, wherein the method comprises administering a stabilized amorphous calcium carbonate to a person in need thereof.

11 Claims, No Drawings

(56) References Cited

FOREIGN PATENT DOCUMENTS

| | | | |
|---|---|---|---|
| KR | 1020050110119 A | 11/2005 | |
| WO | 9724069 A1 | 7/1997 | |
| WO | 9857656 A1 | 12/1998 | |
| WO | 2005025581 A1 | 3/2005 | |
| WO | 2005041921 A2 | 5/2005 | |
| WO | 2005115414 A2 | 12/2005 | |
| WO | 2006043966 A2 | 4/2006 | |
| WO | 2007048811 A1 | 5/2007 | |
| WO | 2008041236 A2 | 4/2008 | |
| WO | 2009053967 A1 | 4/2009 | |
| WO | 2009087553 A1 | 7/2009 | |
| WO | 2012030664 A1 | 3/2012 | |
| WO | 2012149173 A2 | 11/2012 | |
| WO | 2013088440 A1 | 6/2013 | |
| WO | 2014024191 A1 | 2/2014 | |
| WO | 2014122658 A1 | 8/2014 | |
| WO | WO-2014122658 A1 * | 8/2014 | ........... A61K 31/122 |
| WO | 2016016893 A1 | 2/2016 | |
| WO | 2016016895 A1 | 2/2016 | |
| WO | 2016193982 A1 | 12/2016 | |
| WO | 2016193983 A1 | 12/2016 | |
| WO | 2017125917 A1 | 7/2017 | |
| WO | 2017125918 A1 | 7/2017 | |

OTHER PUBLICATIONS

Schepers (1959) Pulmonary histologic reactions to inhaled fiberglas-plastic dust. The American Journal of Pathology 35(6): 1169-1187.
Schneiders et al., (2007) Effect of modification of hydroxyapatite/collagen composites with sodium citrate, phosphoserine, phosphoserine/RGD-peptide and calcium carbonate on bone remodelling. Bone 40(4): 1048-1059.
Shechter et al., (2008) A gastrolith protein serving a dual role in the formation of an amorphous mineral containing extracellular matrix. Proc Natl Acad Sci U S A 105(20): 7129-7134.
Shian et al., (1997) Effect of commercial fortified calcium products on calcium status in rats. Acta Nutrimenta Sinica pp. 333-339. Abstract.
Spiegel et al., (1983) Group therapy and hypnosis reduce metastatic breast carcinoma pain. Psychosomatic Medicine 45(4): 333-339.
Sugawara et al., (2006) Self-organization of oriented calcium carbonate/polymer composites: Effects of a matrix peptide isolated from the exoskeleton of a crayfish. Angew Chem Int Ed Engl 45(18): 2876-2879 with Supporting Information.
Takagi et al., (2000) Immunolocalization of gastrolith matrix protein (GAMP) in the gastroliths and exoskeleton of crayfish, *Procambarus clarkii*. Zoological Science 17: 179-184.
Thomas and Birchall (1983) The retarding action of sugars on cement hydration. Cement and Concrete Research 13(6): 830-842.
Thys-Jacobs et al., (1998) Calcium carbonate and the premenstrual syndrome: Effects on premenstrual and menstrual symptoms. American Journal of Obstetrics and Gynecology 179(2): 444-452.
Tlili et al., (2002) Characterization of CaCO3 hydrates by micro-Raman spectroscopy. Journal of Raman Spectroscopy 33(1): 10-16.
Tolba et al., (2016) High biocompatibility and improved osteogenic potential of amorphous calcium carbonate/vaterite. Journal of Materials Chemistry B 4(3): 376-386.
Travis (1960) The Deposition of Skeletal Structures in the Crustacea. I. The Histology of the Gastrolith Skeletal Tissue Complex and the Gastrolith in the Crayfish, Orconectes (*Cambarus*) Virllis Hagen—Decapoda. Biol Bull 118: 137-149.
Travis (1963) Structural features of mineralization from tissue to macromolecular levels of organization in the decapod Crustacea. Ann N Y Acad Sci 109: 177-245.
Tsutsui et al., (1999) Cloning and expression of a cDNA encoding an insoluble matrix protein in the gastroliths of a crayfish, *Procambarus clarkia*. Zoological Science (Tokyo) 16(4): 619-628.
Ueno and Mizuhira (1984) Calcium transport mechanism in crayfish gastrolith epithelium correlated with the molting cycle. II. Cytochemical demonstration of Ca2+-ATPase and Mg2+-ATPase. Histochemistry 80(3): 213-217.

Väisänen (2011) CaCO3 scale inhibition in paper making processes—evaluation of testing methods and inhibitor performance. Master of Science Thesis. 103 pages.
Withnall (2000) Biology of Yabbies (*Cherax destructor*), Aquaculture Information Notes, Department of Primary Industries, 4 pages.
Wolf and Günther (2001) Thermophysical investigations of the polymorphous phases of calcium carbonate. Journal of Thermal Analysis and Calorimetry 65(3): 687-698.
Xu et al., (2005) Stable amorphous CaCO3 microparticles with hollow spherical superstructures stabilized by phytic acid. Advanced Materials 17(18): 2217-2221.
Xurong et al., (2008) Amorphous Calcium Carbonate in Biomineralization. Progress in Chemistry 20(1): 54-59. Translated abstract.
Yudkovsky et al., (2007) Hepatopancreatic multi-transcript expression patterns in the crayfish *Cherax quadricarinatus* luring the moult cycle. Insect Molecular Biology 16(6): 661-674.
Database Uniprot P98157 (1996) Internet site http://www.uniprot.org/uniprot/P98157.html—last modified Nov. 30, 2010—22 pages.
Database WPI Week 200432 Thomson Scientific, London, GB; AN 343036 XP002512142 & JP 2004 081739 A (Bankoku Needle MFG) Mar. 18, 2004 (Mar. 18, 2004) & JP 2004 081739 A (Akashi Mitsuru; Tabata Masashi; Biomedical Technology Hybrid L) Mar. 18, 2004 (Mar. 18, 2004).
GenCore Database, (2012) DQ847548. 3 pages.
Huxley, "The natural history of the common crayfish" in the Crayfish: An Introduction to the Study of Zoology, Chapter 1, pp. 1-45 and reprinted as 20 HTML sheets, 1879.
Hypocalcemia; Section 12: Endocrine and Metabolic Disorders. In: The Merck Manual of Diagnosis and Therapy, 18th edition. Mark H. Beers (Editor-in-Chief), Robert S. Porter (Editor), Thomas V. Jones (Associate Editor), Justin L. Kaplan (Senior Assistant Editor) and Michael Berkwits (Assistant Editor). Merck Research Laboratories, Division of Merck & Co., Inc.; Whitehouse Station, NJ; 2006, pp. 1250-1254. And Merck Manual 18th Edition Japanese Edition, 2006, pp. 1319-1323.
Medical News Today, Lymphoma and Leukemia, retrieved from internet: https://www.medicalnewstoday.com/categories/lymphoma-leukemia; https://web.archive.org/web/20160930210913/http://www.medicalnewstoday.com/articles/146136.php Sep. 30, 2016 (Sep. 30, 2016); 14 pages.
Melanoma skin cancer. American Cancer Society 2013. 3 pages.
Merck manual of diagnosis and therapy 17th edition 1999 pp. 1979-1982.
Non-Hodgkin lymphoma. American Cancer Society 2012. 5 pages.
Occupational Safety and Health Administration (OSHA), 1995; Occupational Safety and Health Guideline for Calcium Carbonate. U.S. Department of Health and Human Services and U.S. Department of Labor; 7 pages.
Osteoporosis: How to strengthen your bones and prevent fractures. The Healthier Life. 2005. 3 pages.
OsteoPhase. Tango advanced Nutrition—Healthy Bone Support Formula 2011. 3 pages.
Addadi et al., (2003) Taking advantage of disorder: amorphous calcium carbonate and its roles in biomineralization. Advanced Materials 15(12): 959-970.
Akamatsu, "Oriental Drugs, New Revision", 1st Ed. Ishiyaku Shuppan K. K., 1970, p. 911. English translation.
Akiva-Tal et al., (2011) In situ molecular NMR picture of bioavailable calcium stabilized as amorphous CaCO3 biomineral in crayfish gastroliths. Proc Natl Acad Sci USA 108(36): 14763-14768.
Amjad and Hooley (1994) Effect of antiscalants on the precipitation of calcium carbonate in aqueous solutions. Tenside, Surfactants, Detergents 31(1): 12-17.
Bajpai et al., (2004) Pseudohypoparathyroidism Presenting with Bony Deformities Resembling Rickets. Indian Journal of Pediatrics 71(4): 345-347.
Ben-Aharon et al., (2013) Bisphosphonates in the adjuvant setting of breast cancer therapy—effect on survival: a systematic review and meta-analysis. PloS one 8(8): e70044; 9 pages.
Bentov et al., (2010) Stabilization of amorphous calcium carbonate by phosphate rich organic matrix proteins and by single phosphoamino acids. Journal of Structural Biology 171(2): 207-215.

(56) References Cited

OTHER PUBLICATIONS

Buehrer and Reitemeier, (1940) The Inhibiting Action of Minute Amounts of Sodium Hexametaphosphate on the Precipitation of Calcium Carbonate from Ammoniacal Solutions. II. Mechanism of the Process, with Special Reference to the Formation of Calcium Carbonate Crystals. The Journal of Physical Chemistry 44(5): 552-574.
Chen et al., (2013) Ethanol assisted synthesis of pure and stable amorphous calcium carbonate nanoparticles. Chemical Communications 49(83): 9564-9566.
Chick and Borah (1990) Calcium carbonate gel therapy for hydrofluoric acid burns of the hand. Plastic and Reconstructive Surgery 86(5): 935-940.
Clarkson et al., (1992) Role of metastable phases in the spontaneous precipitation of calcium carbonate. Journal of the Chemical Society, Faraday Transactions 88(2): 243-249.
Fujita, "Osteoporosis drugs" Chiryo 72: 455-459, 1990. English translation.
Gal et al., (1996) Calcium carbonate solubility: a reappraisal of scale formation and inhibition. Talanta 43(9): 1497-1509.
Glimcher (1984) Recent studies of the mineral phase in bone and its possible linkage to the organic matrix by protein-bound phosphate bonds. Philos Trans R Soc Lond B Biol Sci 304(1121): 479-508.
Halloran and Donachy (1995) Characterization of organic matrix macromolecules from the shells of the Antarctic scallop, *Adamussium colbecki*. Comp Biochem Physiol B Biochem Mol Biol 111(2): 221-231.
Hecker et al., (2003) Phosphorylation of serine residues is fundamental for the calcium-binding ability of Orchestin, a soluble matrix protein from crustacean calcium storage structures. FEBS Lett 535(1-3): 49-54.
Hu et al., (2004) Effect of calcium supplements on osteoporosis by using nuclear analytical techniques. J Radioanalytical & Nuclear Chemistry 259: 369-373.
Hu et al., (2010) Strongly bound citrate stabilizes the apatite nanocrystals in bone. Proc Natl Acad Sci USA 107(52): 22425-22429.
Huang et al., (2007) A carbonate controlled-addition method for amorphous calcium carbonate spheres stabilized by poly (acrylic acid) s. Langmuir 23(24): 12086-12095.
Inoue et al., (2001) Purification and structural determination of a phosphorylated peptide with anti-calcification and chitin-binding activities in the exoskeleton of the crayfish, *Procambarus clarkii*. Biosci Biotechnol Biochem 65(8): 1840-1848.
Inoue et al., (2007) Significance of the N- and C-terminal regions of CAP-1, a cuticle calcification-associated peptide from the exoskeleton of the crayfish, for calcification. Peptides 28(3): 566-573.
Ishii et al., (1998) Solubilization and Chemical Characterization of an Insoluble Matrix Protein in the Gastroliths of a Crayfish, *Procambarus clarkii*, Biosci Biotechnol Biochem, vol. 62(2): 291-296 4 pages.
Johnsson et al., (1991) Adsorption and mineralization effects of citrate and phosphocitrate on hydroxyapatite. Calcif Tissue Int 49(2): 134-137.
Kavanagh et al., (1990) Inhibitor effects on calcite growth at low supersaturations. Journal of the Chemical Society, Faraday Transactions 86(6): 965-972.
Komuro (1996) Treatment manual for renal disease VIII. 313. Calcium preparations. Kidney and Dialysis Special Edition 41: 871-872. English translation.
Lee et al., (2005) Fabrication of unusually stable amorphous calcium carbonate in an ethanol medium. Materials Chemistry and Physics 93(2-3): 376-382.
Lin and Singer (2005) Inhibition of calcite crystal growth by polyphosphates. Water Research 39(19): 4835-4843.
Lin et al., (2015) Effects of Chalk Use on Dust Exposure and Classroom Air Quality. Aerosol and Air Quality Research 15: 2596-2608.
Loste et al., (2003) The role of magnesium in stabilising amorphous calcium carbonate and controlling calcite morphologies. Journal of Crystal Growth 254(1-2): 206-218.

Luquet and Marin (2004) Biomineralisations in crustaceans: storage strategies. Comptes Rendus Palevol 3(6-7): 515-534.
Ma et al., (2007) A novel extrapallial fluid protein controls the morphology of nacre lamellae in the pearl oyster, *Pinctada fucata*. J Biol Chem 282(32): 23253-23263.
Malkaj and Dalas (2007) The effect of acetaminophen on the crystal growth of calcium carbonate. J Mater Sci Mater Med 18(5): 871-875.
Manoli and Dalas (2002) The effect of sodium alginate on the crystal growth of calcium carbonate. J Mater Sci Mater Med 13(2): 155-158.
Manor et al., (2002) Intensification of redclaw crayfish *Cherax quadricarinalus* culture II. Growout in a separate cell system. Aquacultural Engineering 26: 263-276.
Martins et al., (2008) Hydroxyapatite micro- and nanoparticles: nucleation and growth mechanisms in the presence of citrate species. J Colloid Interface Sci 318(2): 210-216.
Maruyama et al., (2011) Synthesizing a composite material of amorphous calcium carbonate and aspartic acid. Materials Letters 65(2): 179-181.
Meiron et al., (2011) Solubility and bioavailability of stabilized amorphous calcium carbonate. Journal of Bone and Mineral Research 26(2): 364-372.
Müller et al., (2015) Nonenzymatic Transformation of Amorphous CaCO3 into Calcium Phosphate Mineral after Exposure to Sodium Phosphate in Vitro: Implications for in Vivo Hydroxyapatite Bone Formation. ChemBioChem, 16(9): 1323-1332.
Multigner et al., (1983) Pancreatic stone protein, a phosphoprotein which inhibits calcium carbonate precipitation from human pancreatic juice. Biochemical and Biophysical Research Communications 110(1): 69-74.
Nagasawa and Ishii (1996) The chemical structure of insoluble organic matrix contained in Procambarus clarkia gastrolith. Kaiyo Monthly 28: 688-693. English translation.
Nakatsuji et al., (2000) Changes in the Amounts of the Molt-Inhibiting Hormone in Sinus Glands during the Molt Cycle of the American Crayfish, *Procambarus clarkii*. Zoolog Sci 17(8): 1129-1136.
Nebel et al., (2008) On the structure of amorphous calcium carbonate—a detailed study by solid-state NMR spectroscopy. Inorganic Chemistry 47(17): 7874-7879.
Oculi cancrorum: very proper for falls and a pleurisy. Ann R Coll Surg Engl. 1957 20(1): 57-58.
Ogino et al., (1988) Effect of Polyamine-N-Polyphosphonic Acid on the Formation and the Transformation of Calcium-Carbonate. Nippon Kagaku Kaishi (6): 899-905. English abstract on p. 905.
Pames and Sagi (2002) Intensification of redclaw crayfish *Cherax quadricarinalus* culture I. Hatchery and nursery system. Aquacultural Engineering 26: 251-262.
Qi et al., (2014) Atp-stabilized amorphous calcium carbonate nanospheres and their application in protein adsorption. Small 10(10): 2047-2056.
Raz et al., (2002) Stable amorphous calcium carbonate is the main component of the calcium storage structures of the crustacean *Orchestia caavimana*. Biol Bull 203: 269-274.
Reddi et al., (1980) Influence of phosphocitrate, a potent inhibitor of hydroxyapatite crystal growth, on mineralization of cartilage and bone. Biochem Biophys Res Commun 97(1): 154-159.
Rodriguez-Blanco et al., (2008) How to make 'stable' ACC: protocol and preliminary structural characterization. Mineralogical Magazine 72(1): 283-286.
Rodriguez-Blanco et al., (2012) The role of pH and Mg on the stability and crystallization of amorphous calcium carbonate. Journal of Alloys and Compounds 536(Supp 1): S477-S479 International Symposium on Metastable, Amorphous and Nanostructured Materials, ISMANAM-2011 (Jun. 26 to Jul. 1, 2011).
McKee (1975) Hypocalcemia in leukemia. South Med J 68(7): 828-832.
"Lymphoma and Leukemia", Medical News Today, Sep. 30, 2016 (Sep. 30, 2016), pp. 1-4, URL: https://web.archive.org/web/

(56) References Cited

OTHER PUBLICATIONS

20160930202858/https://www.medicalnewstoday.com/categories/lymphoma-leukemia, XP009518028.

* cited by examiner

AMORPHOUS CALCIUM CARBONATE FOR TREATING A LEUKEMIA

FIELD OF THE INVENTION

The present invention relates to compositions and methods of treating leukemia, and in particular chronic lymphocytic leukemia, using amorphous calcium carbonate stabilized by at least one stabilizing agent.

BACKGROUND OF THE INVENTION

Chronic lymphocytic leukemia (CLL) is one of the most common types of leukemia in adults. It often occurs during or after middle age and it rarely occurs in children. Usually, CLL does not cause any signs or symptoms and is found during a routine blood test. CLL is commonly staged according to the following scheme: stage 0—increased lymphocytes count (lymphocytosis) and appearance of "basket" cells without any other signs ("basket" or "smudge" cells are essentially neoplastic cells that got "smudged" during slide preparation for routine blood smear because of the fragile nature of these cells); stage I—lymphocytosis and appearance of enlarged lymph nodes; stage II—lymphocytes+ appearance of enlarged liver or spleen and lymph nodes may be enlarged; stage III—lymphocytes+decrease in red blood cells count, the liver, spleen or lymph nodes may be enlarged; and stage IV—lymphocytes+reduced platelets count, lymph nodes, liver, or spleen may be enlarged and the number of red blood cells may be reduced.

Whereas several methods for treating CLL are currently present at advanced stages of the disease, at the early stages of the disease such as stage 0, the treatment is usually a watchful waiting, i.e. closely monitoring patient's condition without providing any treatment until the disease reaches more advanced stage and/or until signs or symptoms appear or change.

Considering the constantly increasing incidence rate of CLL and improved diagnostic tools allowing early diagnosis of the disease, there is an unmet need for new treatments, especially at the early stages of the CLL.

SUMMARY OF THE INVENTION

The present invention relates to methods of treating a leukemia, and in particular chronic lymphocytic leukemia, using compositions comprising stable amorphous carbonate. It has been unexpectedly found that stabilized amorphous calcium carbonate may slow down or stop the development of chronic lymphocytic leukemia (CLL) at its initial stage. This is based on the observation that upon the administration of ACC by a person diagnosed as a zero stage CLL, the level of WBC (leucocytes) ceased elevating for at least three months following the beginning of treatment.

In one aspect, the present invention provides a composition comprising an amorphous calcium carbonate (ACC) for use in treatment of leukemia, wherein the ACC is stabilized by at least one stabilizing agent. In some embodiments, the leukemia is chronic leukemia and acute leukemia. In other embodiments, the chronic leukemia is selected from chronic lymphocytic leukemia, chronic myelogenous leukemia and Hairy cell leukemia. According to one embodiment, the leukemia is chronic lymphocytic leukemia (CLL). According to certain embodiments, the CLL is at the early stage of the disease. According to some embodiment, the early stage of CLL is a watchful waiting stage. According to another embodiment, the the early stage is stage 0.

In some embodiments, the leukemia is an acute leukemia selected from acute myeloid leukemia and acute lymphoblastic leukemia.

According to certain embodiments, the ACC is selected from a natural ACC and synthetic ACC.

According to one embodiment, the ACC is a synthetic ACC. According to such embodiments, the ACC is stabilized by at least one stabilizer. According to some embodiments, the stabilizer is selected from polyphosphate, organic acid, phosphorylated amino acid, bisphosphonate, phosphorylated organic acid, phosphoric or sulfuric esters of hydroxy carboxylic acid, hydroxyl bearing organic compound combined with alkali hydroxides, and any combination thereof. According to other embodiment, the polyphosphate is an inorganic polyphosphate selected from triphosphate, pyrophosphate and hexametaphosphate; the phosphorylated amino acid is selected from phosphoserine or phosphothreonine; the organic acid is selected from citric acid and tartaric acid; and the bisphosphonate is selected from alendronate, etidronic acid, zoledronic acid and medronic acid.

According to some embodiments, the treatment of a leukemia comprises at least one of the following: ceasing, retarding, preventing and reversing the development of the leukemia. According to some embodiments, ceasing, retarding or preventing the development of the leukemia comprises ceasing or retarding the progression of lymphocytosis.

According to other embodiments the treatment of a leukemia comprises administering about 500 mg/day to about 5000 mg/day of ACC. According to some embodiments, the composition is orally administered.

According to one embodiment, the present invention provides a composition comprising an amorphous calcium carbonate stabilized by at least one stabilizer, for use in treating a chronic lymphocytic leukemia. According to some embodiments, the chronic lymphocytic leukemia is at stage 0 or at stage I of the disease. According to one embodiment, the stabilizer is selected from phosphoserine, triphosphate, citric acid, a combination of phosphoserine and citric acid and a combination of triphosphate and citric acid.

According to some embodiments of the invention, the composition is formulated as a pharmaceutical composition, a nutraceutical composition, a food supplement or a medical food.

According to some embodiments, the present invention provides a pharmaceutical composition comprising an amorphous calcium carbonate, for use in treating a chronic lymphocytic leukemia at stage 0, wherein the ACC is stabilized by a stabilizer selected from phosphoserine, triphosphate, citric acid, a combination of phosphoserine and citric acid, and a combination of triphosphate and citric acid.

According to another aspect, the present invention provides a method of treating a leukemia in a subject in need thereof comprising administering a composition comprising an effective amount of amorphous calcium carbonate (ACC) stabilized by at least one stabilizing agent. According to some embodiments, the leukemia is a chronic leukemia selected from the group consisting of chronic lymphocytic leukemia, chronic myelogenous leukemia, and Hairy cell leukemia, or an acute leukemia selected from the group consisting of acute myeloid leukemia and acute lymphoblastic leukemia. According to some embodiments, the present invention provides a method of treating chronic lymphocytic leukemia. According to one embodiment, the chronic leukemia is at stage 0 of the disease.

According to some embodiments, the method of treating leukemia comprises at least one of: ceasing, retarding or preventing the development of the leukemia. According to some embodiments ceasing, retarding or preventing the development of the leukemia comprises ceasing or retarding the progression of lymphocytosis. According to some embodiments, ceasing the progression of lymphocytosis comprises maintaining the level of white blood cells at the same level for at least 3 months.

According to other embodiment, the method comprises administering about 500 mg/day to about 5000 mg/day of ACC.

According to some embodiments, the composition comprising ACC and at least stabilizer is formulated as a pharmaceutical composition or nutraceutical composition, a food supplement or a medical food.

DETAILED DESCRIPTION OF THE INVENTION

The present invention relates to compositions and methods for treatment of a leukemia. It has been surprisingly found, according to the present invention, that stable amorphous calcium carbonate (ACC) may successfully slow down or even prevent further development of the chronic lymphocytic leukemia. Even more unexpected observation was that the progression of the disease had been inhibited at the very early stage of the disease, at which the common acceptable treatment is watchful waiting.

According to one aspect, the present invention provides a composition comprising an amorphous calcium carbonate (ACC) for use in treatment of a leukemia, wherein the ACC is stabilized by at least one stabilizing agent.

The terms "treating" and "treatment" are uses herein interchangeably and refer to taking steps to obtain beneficial or desired results, including clinical results. Beneficial or desired clinical results include, but are not limited to, alleviation or amelioration of one or more symptoms associated with leukemia and in particular chronic lymphocytic leukemia, delay or slowing the development or the progression of leukemia, amelioration, palliation or stabilization of the disease, and other beneficial results. In particular, according to one embodiment, treating a leukemia comprises at least one of the following: ceasing, retarding reversing and preventing the development of the leukemia.

The term "leukemia" refers to a cancer of white blood cells (WBC) involving bone marrow and circulating WBCs, and of organs such as the spleen and lymph nodes. According to one embodiment, the leukemia is a chronic leukemia. According to some embodiments, the chronic leukemia is selected from chronic lymphocytic leukemia, chronic myelogenous leukemia, and Hairy cell leukemia. According to other embodiments, the leukemia is an acute leukemia. According to some embodiments, the acute leukemia is selected from acute myeloid leukemia and acute lymphoblastic leukemia.

According to some embodiments, the leukemia is a chronic leukemia. Thus, according to one embodiment, the present invention provides a composition comprising an ACC stabilized by at least one stabilizing agent for use in treatment of chronic leukemia According to one embodiment, the leukemia is a chronic lymphocytic leukemia (CLL). CLL is commonly staged according to the following scheme: stage 0—increased lymphocytes count (lymphocytosis) and appearance of "basket" cells without any other signs; stage I—lymphocytosis and appearance of enlarged lymph nodes; stage II—lymphocytes+appearance of enlarged liver or spleen and lymph nodes may be enlarged, stage III—lymphocytes+decrease in red blood cells count, the liver, spleen or lymph nodes may be enlarged; and stage IV—lymphocytes+reduced platelets count, lymph nodes, liver, or spleen may be enlarged and the number of red blood cells may be reduced. In one embodiment, CLL is at stage 0, stage I, stage II, stage III or at stage IV of the disease.

According to another embodiment, the CLL is at the early stage of the disease. According to one embodiment, the early stage is a watchful waiting stage, i.e. the stage at which watchful waiting treatment is commonly recommended. According to another embodiment, the early stage is stage 0 of CLL. According to another embodiment, the early stage is stage I of CLL.

The terms "amorphous calcium carbonate", "ACC", "stable ACC" and "stabilized ACC" are used herein interchangeably and refer to the amorphous form of calcium carbonate. The term "stable" as used herein indicates that the calcium carbonate is maintained in the amorphous form for a long period of time, for example for about at least 7 days in the solid form having less than or about 30% crystalline calcium carbonate. According to any one of the above embodiments, the composition is stable for at least 7 days. According to some embodiments, the composition is stable for at least 1 month. According to other embodiments, the composition is stable for at least 3 months. According to a further embodiment, the composition is stable for 6 months. According to certain embodiments, the composition is stable for at least 1 year. According to a particular embodiment, the composition is stable to at least 2 years.

According to any one of the above embodiments, the ACC stabilized by at least one stabilizer is a natural ACC. The term "natural ACC" as used herein refers to any ACC isolated or derived from a natural source. Non-limiting examples of natural sources of ACC include gastroliths of freshwater crustaceans. In certain embodiments, the naturally occurring ACC source includes gastrolith organs, or a portion thereof ground to a fine powder, essentially as described in WO 2005/115414. Optionally, ACC comprises a combination of naturally occurring and synthesized ACC.

According to another embodiment, the ACC is a synthetic ACC. The term "synthetic ACC" as used herein generally refers to any ACC produced by man ex-vivo. According to some embodiments, the ACC is a synthetic ACC stabilized by at least one stabilizer as defined herein below.

The terms "stabilizing agent" and "stabilizer" are used herein interchangeably and refer to any substance that contributes to preserving calcium carbonate in the amorphous state during ACC production, formulating and/or storage. In certain embodiments, the stabilizing agent is a single agent. In other embodiments, use of several stabilizing agents is encompassed.

ACC Stabilizers

The stabilizer may comprise a molecule having one or more functional groups selected from, but not limited to, hydroxyl, carboxyl, ester, amine, phosphino, phosphono, phosphate, sulfonyl, sulfate or sulfino groups. The hydroxy bearing compounds, combined with the hydroxide, optionally also bear other functions like carboxyl, etc. but with the hydroxyl not being esterified.

According to some embodiments, the stabilizer has low toxicity or no toxicity to mammalian cells or organism, and in particular to a human being. According to some embodiments, the stabilizer is of food, nutraceutical or pharmaceutical grade.

In certain embodiments, the ACC stabilizing agent is independently at each occurrence, an organic acid, phosphorylated, phosphonated, sulfated or sulfonated organic compound, phosphoric or sulfuric ester of a hydroxyl carboxylic acid, an organoamine compound, an organic compound comprising a hydroxyl, an organophosphorous compound or a salt thereof, phosphorylated amino acids and derivatives thereof, a bisphosphonate compound, an organophosphate compound, an organophosphonate compound, an inorganic phosphorous acid, an organic compound having multiple functional groups as defined above, an inorganic phosphate and polyphosphate compound, an organic compound having a polyphosphate chain, an organic surfactant, a bio-essential inorganic ion, or any combination thereof.

According to some embodiments, the stabilizer is an organic acid. According to certain embodiments, the organic acid is selected from ascorbic acid, citric acid, lactic acid, acetic acid, oxalic acid, malonic acid, glutaconic acid, succinic acid, maleic acid, lactic acid, aconitic acid, and optionally include compounds having at least two carboxylic groups and molecular weight not larger than 250 g/mol, such as citric acid, tartaric acid, malic acid, etc. According to one particular embodiment, the stabilizer is citric acid.

In another embodiment, the phosphoric ester of hydroxyl carboxylic acids is a phosphoenolpyruvate. In another embodiment, the phosphoric or sulfuric esters of hydroxyl carboxylic acids comprise amino acids, e.g. phosphorylated amino acids. Examples of such esters are phosphoserine, phosphothreonine, sulfoserine, sulfothreonine and phosphocreatine.

The hydroxyl bearing compounds combined with hydroxide may comprise, for example, mono-, di- tri-, oligo-, and polysaccharides like sucrose or other polyols like glycerol. The hydroxyl bearing compounds may further comprise hydroxy acids like citric acid, tartaric acid, malic acid, etc., or hydroxyl-bearing amino acids such as serine or threonine. Each possibility represents a separate embodiment, of the present invention.

Some specific unlimited examples for such ACC stabilizers include phytic acid, citric acid, sodium pyrophosphate dibasic, adenosine 5'-monophosphate (AMP) sodium salt, adenosine 5'-diphosphate (ADP) sodium salt and adenosine 5'-triphosphate (ATP) disodium salt hydrate, phosphoserine, phosphorylated amino acids, food grade surfactants, sodium stearoyl lactylate, and combinations thereof.

According to some embodiments, the stabilizer comprises at least one component selected from phosphoric or sulfuric esters of hydroxyl carboxylic acids, such as phosphoenolpyruvate, phosphoserine, phosphorthreonine, sulfoserine or sulfothreonine and hydroxyl bearing organic compounds, selected from mono-, di-, tri-, oligo- and polysaccharides, for example, sucrose, mannose, glucose. The hydroxyl bearing compound may further comprise at least one alkali hydroxide, such as sodium hydroxide, potassium hydroxide and the like. The phosphorylated acids may be present in oligopeptides and polypeptides. In other embodiments, of the invention, the stabilizer is an organic acid selected from monocarboxylic acid or multiple carboxylic acid, e.g. dicarboxylic acid or tricarboxylic acid. Each possibility represents a separate embodiment, of the invention. The organic acid may be as defined above.

In some embodiments, of the invention, the ACC stabilizer is selected from phosphorylated amino acids, polyols and combinations thereof. In some embodiments, the stable ACC comprises a phosphorylated compound as a stabilizer wherein the phosphorylation is performed on the hydroxyl group of an organic compound. In some embodiments, the stable ACC comprises a stabilizer selected from the group consisting of citric acid, phosphoserine, phosphothreonine and combinations thereof. The non-limiting examples of stabilizers containing phosphate, phosphite, phosphonate groups and salts or esters thereof include phytic acid, dimethyl phosphate, trimethyl phosphate, sodium pyrophosphate, tetraethyl pyrophosphate, ribulose bisphosphate, etidronic acid and other medical bisphosphonates, 3-phosphoglyceric acid salt, glyceraldehyde 3-phosphate, 1-deoxy-D-xylulose-5-phosphate sodium salt, diethylene triamine pentakis(methylphosphonic acid), nitrilotri(methylphosphonic acid), 5-phospho-D-ribose 1-diphosphate pentasodium salt, adenosine 5'-diphosphate sodium salt, adenosine 5'-triphosphate disodium salt hydrate, α-D-galactosamine 1-phosphate, 2-phospho-L-ascorbic acid trisodium salt, α-D-galactose 1-phosphate dipotassium salt pentahydrate, α-D-galactosamine 1-phosphate, O-phosphorylethanolamine, disodium salt hydrate, 2,3-diphospho-D-glyceric acid pentasodium salt, phospho(enol)pyruvic acid monosodium salt hydrate, D-glyceraldehyde 3-phosphate, sn-glycerol 3-phosphate lithium salt, D-(−)-3-phosphoglyceric acid disodium salt, D-glucose 6-phosphate sodium salt, phosphatidic acid, ibandronate sodium salt, phosphonoacetic acid, DL-2-amino-3-phosphonopropionic acid or combinations thereof. The bio-essential inorganic ions may include, inter alia, Na, K, Mg, Zn, Fe, P, S, N, P or S in the phase of oxides, or N as ammonia or nitro groups.

According to some embodiments, the stabilizer is a polyphosphate or pharmaceutically acceptable salts thereof. According to some embodiments, the polyphosphate is physiologically compatible, water soluble polyphosphate salt selected from the group consisting of sodium, potassium and any other essential cation of polyphosphate. In one embodiment, the polyphosphate is organic or inorganic polyphosphate. The term "polyphosphate" as used herein refers to polymeric esters of PO4. According to some embodiments, the polyphosphate is physiologically compatible water soluble polyphosphate salt selected from the group consisting of sodium and potassium polyphosphate. In some embodiments, the polyphosphate is an inorganic polyphosphate or pharmaceutically acceptable salts thereof. Not-limiting examples of such salt are Na, K, Mg, Mn and Zn. According to some embodiments, the inorganic phosphate comprise 2 to 10 phosphate groups, e.g. 2, 3, 4, 5, 6, 7, 8, 9, or 10 phosphate group. According to some embodiments, the polyphosphate is selected from pyrophosphate, triphosphate, and hexametaphosphate. According to one embodiment, the stabilizer is pyrophosphate or pharmaceutically acceptable salts thereof such as sodium pyrophosphate. According to another embodiment, the stabilizer is triphosphate or pharmaceutically acceptable salts thereof such as sodium triphosphate. The term "triphosphate" and "tripolyphosphate" are used herein interchangeably. According to a further embodiment, the stabilizer is hexametaphosphate or a pharmaceutically acceptable salt thereof such sodium hexametaphosphate.

According to some embodiments, the stabilizer is a bisphosphonate or pharmaceutically acceptable salts thereof. The not-limiting examples of salt are Na, K, Mg, Mn and Zn.

The term "bisphosphonate" as used herein refers to organic compounds having two phosphonate (PO(OH)2) groups. The term further relates to compounds having a backbone of PO3-organic-PO3. Most typical is a series of bisphosphonates that are used as pharmaceuticals for treating osteoporosis. According to some embodiments, the bisphosphonate is selected from the group consisting of etidronic acid, zoledronic acid, medronic acid, alendronic acid and a pharmaceutically acceptable salt thereof. According to some embodiments, the stabilizer is an etidronic acid or a pharmaceutically acceptable salt thereof. According to another embodiment, the stabilizer is a zoledronic acid or a pharmaceutically acceptable salt thereof. According to a further embodiment, the stabilizer is a medronic acid or a pharmaceutically acceptable salt thereof. According to certain embodiments, the stabilizer is alendronic acid or a pharmaceutically acceptable salt thereof.

According to certain embodiments, the stabilizer is a phosphorylated amino acid. According to one embodiment, the phosphorylated amino acid is phosphoserine. According to another embodiment, the phosphorylated amino acid is phosphothreonine.

According to some embodiments, the stabilizer is polyphosphate or a bisphosphonate as defined hereinabove, and the molar ratio between P atoms of the stabilizer and Ca atoms of the ACC (P:Ca molar ratio) is about 1:90 to 1:1. In one embodiment, the P:Ca molar ratio is about 1:40 to about 1:1. In a further embodiment, the P:Ca molar ratio is about 1:35 to about 1:2. In certain embodiments, the P:Ca molar ratio is about 1:30 to about 1:3. In certain embodiments, the P:Ca molar ratio is about 1:28 to about 1:3. In other embodiment, the P:Ca molar ratio is about 1:25 to about 1:4. In further embodiment, the P:Ca molar ratio is about 1:20 to about 1:5. In another embodiment, the P:Ca molar ratio is about 1:20 to about 1:6. In a particular embodiment, the P:Ca molar ratio is about 1:15 to about 1:5. In another particular embodiment, the P:Ca molar ratio is about 1:25 to about 1:5. According to some embodiments, such polyphosphate is pyrophosphate, triphosphate, hexametaphosphate or a pharmaceutically acceptable salt thereof. According to another embodiment, the bisphosphonate is alendronic acid, etidronic acid, zoledronic acid or medronic acid and the P:Ca molar ratio is as defined hereinabove.

According to some embodiments, the calcium content (Ca content) of such compositions comprising polyphosphate or bisphosphonate as a stabilizer is about 1 wt % to about 39 wt %, about 5 wt % to about 39 wt %, about 10% to about 39 wt %, about 15% to about 39 wt %, about 20 wt % to about 38 wt %, about 25 wt % to about 38 wt %, or about 30 to about 38. The terms "Ca content" and "calcium content" is used herein interchangeably and refer to the content of calcium of the ACC in the final composition.

In certain embodiments, the P:Ca molar ratio is about 1:40 to about 1:1, and the Ca content is about 20 wt % to about 39 wt %. In some embodiments, the molar ratio is 1:28 to about 1:3, and the Ca content is about 30 wt % to about 38 wt %. In another embodiment, the molar ratio is 1:25 to about 1:5, and the Ca content is about 30 wt % to about 36 wt %.

According to some embodiments, the stabilizer is selected from the group consisting of a polyphosphate, phosphorylated amino acid, bisphosphonate, citric acid, tartaric acid and any combination thereof. According to one embodiment, the polyphosphate is selected from the group consisting of triphosphate, pyrophosphate, and hexametaphosphate, the phosphorylated amino acid is phosphoserine or phosphothreonine, and the bisphosphonate is selected from the group consisting of alendronate, etidronic acid, zoledronic acid and medronic acid.

According to some embodiments, the stabilizer is polyphosphate or bisphosphonate and the molar ratio between P atoms of the stabilizer and Ca atoms of the ACC is about 1:90 to 1:1.

The stabilized ACC may be stabilized by more than one stabilizers. In some embodiments, two or more stabilizers, e.g. 2, 3 or 4 stabilizers are added. In some embodiments, the first stabilizer and the second stabilizer are similar In other embodiments, the first stabilizer and the second stabilizer are different stabilizers. The first and the second stabilizers may be each independently as defined hereinabove. The stable ACC can comprise more than two stabilizers, wherein one or more stabilizers are added to the ACC during the formation and precipitation of the ACC.

According to one embodiment, ACC is stabilized by a combination of phosphoserine and citric acid. According to another embodiment, ACC is stabilized by a combination of triphosphate and citric acid.

According to any one of the above embodiments, the stabilized ACC is present is the form of a powder. According to some embodiments, the particles of the ACC in the powder have a particle size of less than about 100 µm. In some embodiments, the ACC particles have a particle size of about 100 µm to about 5 µm. In other embodiments, the particle size is about 50 µm to about 5 µm, or about 30 to about 5 µm. In one particular embodiments the particles having the size less than 50 µm, less than 40 µm, less than 30 µm, less than 20 µm or less than 10 µm. According to some embodiments at least 70%, at least 80% or at least 90% of the ACC particles have the particle size of less than 5 µm.

The term "particle" as used herein refers to a discrete microparticle or a nanoparticle of ACC stabilized by the stabilizer as defined hereinabove, as well as to the aggregates or agglomerates thereof. According to some embodiments, the particles are primary particles of the stabilized ACC. The basic nanoparticles are in the range of 5 to 500 nm or 10 to 300 nm or 20 to 100 nm. These nanoparticles immediately agglomerate and aggregate into much larger secondary particles. These aggregation and agglomeration can be then broken by milling and dissolution techniques into smaller particles. According to other embodiments the particles are agglomerates or aggregates of the primary particles, i.e. secondary particles.

According to any one of the above embodiments, the term treating a leukemia comprises at least one of the following: ceasing, retarding preventing or reversing the development of the leukemia. According to one embodiment, treating a leukemia comprises ceasing the development of the leukemia. The development of the disease is characterized by change in at least one of the parameters associated with or characterizing leukemia. According to some embodiments, treating a leukemia comprises retarding the development of the leukemia. According to a further embodiment, treating a leukemia comprises preventing the development of the leukemia. According to one embodiment, the leukemia is CLL. Thus, in one embodiment, treating CLL comprises ceasing, retarding or preventing the development of CLL. The development of the disease is characterized by a change in at least one of parameters associated or characterizing CLL. Non-limiting examples for such parameters are increase in WBC count (lymphocytosis), appearance of "basket" cells, appearance of enlarged lymph nodes liver and/or spleen, reduction in red blood cells (RBC) count, and reduction in platelets count. Thus, ceasing, retarding or slowing down a change in any one of these parameters is considered to or indicates for ceasing, retarding, slow down or preventing the development of CLL. According to one embodiment, treating of CLL comprises ceasing, retarding or preventing development of CLL at early stages of the disease. According to a further embodiment, the early stage is stage 0. According to another embodiment, the early stage is stage I. In certain embodiments, treating of CLL comprises treating at stage 0 and/or at stage I. According to one embodiment, treating CLL, e.g. ceasing, retarding preventing or reversing the development of the CLL comprises ceasing, retarding or reversing the progression of lymphocytosis. According to some embodiments, retarding or reversing the progression of lymphocytosis comprises maintaining the level of lymphocyte at the same level for at least 2 months. According to another embodiment, retarding or reversing the progression of lymphocytosis comprises maintaining the level of lymphocyte at the same level for at least 3, 4, 5, 6, 9 or 12 months. According to another embodiment, treating CLL comprises preventing the appearance, ceasing or retarding the progression of appearance of "basket" cells, or reduction in the number of "basket" cells. According to another embodiment, treating the CLL comprises preventing the appearance of enlarged lymph nodes liver and/or spleen; or ceasing or retarding the enlargement of lymph nodes liver and/or spleen. According to one embodiment, treating the CLL comprises obtaining a decrease in the size of the enlarged lymph nodes liver and/or spleen. According to one embodiment, the decrease in the size is of 10%, 20%, 30%, 40% or 50%. According to another embodiment, treating CLL comprises preventing, ceasing or retarding the decrease in RBC count, platelets count or both. According to some embodiments, ceasing or retarding the decrease in RBC count, platelets count or both comprises maintaining the level of RBC, platelets or both at the same level for at least 2, 3, 4, 5, 6, 9 or 12 months. According to a further embodiment, treating CLL comprises increase in RBC count and/or in platelets count. Monitoring the development of the CLL and in particular the parameters characterizing CLL, may be obtained by any known method.

The composition for use of the present invention may be administered by any known method. The terms "administering" or "administration of" the composition of the present invention can be carried out using one of a variety of methods known to those skilled in the art. For example, the composition may be administered enterally or parenterally. Enterally refers to administration via the gastrointestinal tract including per os, sublingually or rectally. Parenteral administration includes administration intravenously, intradermally, intramuscularly, intraperitoneally, subcutaneously, ocularly, sublingually, intranasally, by inhalation, intraspinally, intracerebrally, and transdermally (by absorption, e.g., through a skin duct). The composition of the present invention can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods. In some aspects, the administration includes both direct administration, including self-administration, and indirect administration, including the act of prescribing a drug or a medical food. For example, as used herein, a physician who instructs a patient to self-administer a drug or a medical food, or to have the drug or the medical food administered by another and/or who provides a patient with a prescription for a drug or a medical food is administering the drug or a medical food to the patient.

In one embodiment, the composition of the present invention is administered via a systemic administration. For example, the composition of the present invention may be administered orally, sublingually or rectally. Alternatively the composition of the present invention may be administered intravenously, intradermally, intramuscularly, intraperitoneally, subcutaneously, ocularly, sublingually, intranasally, by inhalation, intraspinally, intracerebrally, and transdermally. In one specific embodiment, the composition of the present invention is administered orally.

According to any one of the above embodiments, treating leukemia comprises administering about 500 mg/day to about 5000 mg/day, about 750 mg/day to about 4000 mg/day of ACC, about 1000 mg/day to about 3000 mg/day, or about 1500 mg/day to about 2500 mg/day of stabilized ACC. According to one embodiment, treating leukemia comprises administering about 500 mg/day to about 3000 mg/day or about 1000 mg/day to about 2500 mg/day of stabilized ACC. According to one embodiment, the leukemia is CLL.

According to any one of the above embodiments, the composition of the present invention is formulated as a pharmaceutical composition, nutraceutical composition, a food supplement or a medical food.

According to one embodiment, the composition comprising a stabilized ACC for use in treatment of a leukemia is a pharmaceutical composition. According to another embodiment, the composition comprising a stabilized ACC for use in treatment of a leukemia is a nutraceutical composition. According to yet another embodiment, the composition comprising a stabilized ACC for use in treatment of a leukemia is a food supplement. According to a further embodiment, the composition comprising a stabilized ACC for use in treatment of a leukemia is a medical food. According to such embodiments, the leukemia is CLL. According to another embodiment, the CLL is at stage 0 or stage I of the disease.

The term "pharmaceutical composition" as used herein refers to any composition comprising a stabilized ACC and a pharmaceutically acceptable excipient.

The term "pharmaceutically acceptable carrier" or "pharmaceutically acceptable excipient" as used herein refers to any and all solvents, dispersion media, preservatives, antioxidants, coatings, isotonic and absorption delaying agents, surfactants, fillers, disintegrants, binders, diluents, lubricants, glidants, pH adjusting agents, buffering agents, enhancers, wetting agents, solubilizing agents, surfactants, antioxidants the like, that are compatible with pharmaceutical administration. The use of such media and agents for pharmaceutically active substances is well known in the art. The compositions may contain other active compounds providing supplemental, additional, or enhanced therapeutic functions.

The terms "pharmaceutically acceptable" and "pharmacologically acceptable" include molecular entities and compositions that do not produce an adverse, allergic, or other untoward reactions when administered to an animal, or human, as appropriate. For human administration, preparations should meet sterility, pyrogenicity, general safety, and purity standards as required by a government drug regulatory agency, e.g., the United States Food and Drug Administration (FDA) Office of Biologics standards.

As used herein, the term "nutraceutical composition" refers to a composition suitable for use in human beings or animals, comprising one or more natural products with therapeutic action which provide a health benefit or have been associated with disease prevention or reduction.

The term "food supplement" is used to mean a product containing said composition and intended to supplement the food by providing nutrients that are beneficial to health according to any acceptable directive, such as European directive. For example, a food supplement may be a capsule or a tablet for swallowing, or a powder or small vial to mix with a food and providing beneficial health effects.

As used herein, the term "medical food" refers to a food item specially formulated for the dietary management of a disease or disorder in a subject.

The composition of the present invention may be formulated as defined hereinabove. In one particular embodiment, the composition comprising a stabilized ACC is formulated as a solid dosage form selected from tablets, capsules, powder or granules. In another embodiment, the composition comprising a stabilized ACC is formulated as a liquid or semi-liquid dosage form selected from an elixir, tincture, suspension, syrup, emulsion or gel. According to a further embodiment, the composition is formulated as a composition for inhalation.

According to certain embodiments, the present invention provides a composition comprising an amorphous calcium carbonate stabilized by at least one stabilizer, for use in treating a leukemia. According to one embodiment, the leukemia is a chronic leukemia such as chronic lymphocytic leukemia, chronic myelogenous leukemia, and Hairy cell leukemia. According to one embodiment, the present invention provides a composition comprising an ACC for use in treatment of CLL, wherein the ACC is stabilized by at least one stabilizing agent. According to one embodiment, the treating comprises treating CLL at stage 0 of the disease. According to another embodiment, the treating comprises treating at stage I of the disease. According to a further embodiment, treating comprises administering about 500 mg/day to about 5000 mg/day, or about 750 mg/day to about 4000 mg/day, about 1000 mg/day to about 3000 mg/day, or about 1500 mg/day to about 2500 mg/day of stabilized ACC. According to some embodiments, the stabilizing agent is selected from the group consisting of a polyphosphate such as triphosphate, pyrophosphate, and hexametaphosphate; phosphorylated amino acid such as phosphoserine or phosphothreonine, bisphosphonate such as alendronate, etidronic acid, zoledronic acid and medronic acid; organic acid such as citric acid and tartaric acid; and any combination thereof. According to one embodiment, treating a leukemia comprises at least one of ceasing, retarding and preventing the development of the leukemia. According to one embodiment, the composition is a pharmaceutical composition. According to another embodiment, the composition is nutraceutical composition or food supplement.

According to one embodiment, the present invention provides a pharmaceutical composition comprising an ACC and a pharmaceutically acceptable excipient, for use in treatment of CLL at stage 0 and/or stage I of the disease, wherein the ACC is stabilized by a stabilizer selected from phosphoserine; triphosphate; citric acid; a combination of phosphoserine and citric acid; and a combination of triphosphate and citric acid. According to one embodiment, the treatment comprises administration of about 500 mg/day to about 5000 mg/day or about 1000 mg/day to about 3000 mg/day of stabilized ACC. According to one embodiment, the pharmaceutical composition is orally administered.

According to one embodiment, the present invention provides a food supplement comprising an ACC, for use in treatment of CLL at stage 0 and/or stage I of the disease, wherein the ACC is stabilized by a stabilizer selected from phosphoserine, triphosphate, citric acid, a combination of phosphoserine and citric acid; and a combination of triphosphate and citric acid. According to one embodiment, the treatment comprises administration of about 500 mg/day to about 5000 mg/day or about 1000 mg/day to about 3000 mg/day of stabilized ACC.

According to one aspect the present invention provides a method of treating a leukemia in a subject in need thereof comprising administering a composition comprising an effective amount of amorphous calcium carbonate (ACC) stabilized by at least one stabilizing agent. According to one embodiment, the leukemia is a chronic leukemia. According to some embodiments, the chronic leukemia is selected from chronic lymphocytic leukemia, chronic myelogenous leukemia, and Hairy cell leukemia. According to other embodiments, the leukemia is an acute leukemia. According to some embodiments, the acute leukemia is selected from acute myeloid leukemia and acute lymphoblastic leukemia.

The term "effective amount" as used herein refers to a sufficient amount of the composition comprising stabilized ACC for treating leukemia at a reasonable benefit/risk ratio applicable to any medical or nutritional treatment.

According to one embodiment, the present invention provides a method of treating CLL in a subject in need thereof comprising administering a composition comprising an effective amount of amorphous calcium carbonate (ACC) stabilized by at least one stabilizing agent as defined above. According to one embodiment, the treating is at the early stages of the disease e.g. at stage 0. According to a further embodiment, the method comprises administering about 500 mg/day to about 5000 mg/day, about 750 mg/day to about 4000 mg/day, about 1000 mg/day to about 3000 mg/day, or about 1500 mg/day to about 2500 mg/day of stabilized ACC. According to one embodiment, treating CLL comprises at least one of the groups consisting of ceasing, retarding and preventing the development of the leukemia. According to some embodiments, treating a CLL comprise as least one of the group ceasing, retarding or reversing the progression of lymphocytosis; ceasing or retarding the progression of appearance of "basket" cells; reduction in the number of "basket" cells; preventing the appearance of enlarged lymph nodes liver and/or spleen; ceasing or retarding the enlargement of lymph nodes liver and/or spleen; decreasing the size of the enlarged lymph nodes liver and/or spleen; preventing, ceasing or retarding the decrease in RBC count; preventing, ceasing or retarding the decrease in platelets count; increase in RBC count; and increase in RBC in platelets count. According to one embodiment, retarding or reversing the progression of lymphocytosis comprises maintaining the level of lymphocyte at the same level for at least 3, 4, 5, 6, 9 or 12 months. According to another embodiment, the decrease in the size of the enlarged lymph nodes liver and/or spleen comprises a decrease of 10%, 20%, 30%, 40% or 50%. According to other embodiments, ceasing or retarding the decrease in RBC count, platelets count or both comprises maintaining the level of RBC, platelets or both at the same level for at least 2, 3, 4, 5, 6, 9 or 12 months. According to some embodiments, the stabilizing agent is selected from the group consisting of a polyphosphate such as triphosphate, pyrophosphate, and hexametaphosphate; phosphorylated amino acid such as phosphoserine or phosphothreonine, bisphosphonate such as alendronate, etidronic acid, zoledronic acid and medronic acid; organic acid such as citric acid and tartaric acid; and any combination thereof. According to any one of the above embodiments, the composition of the present invention is formulated as a pharmaceutical or nutraceutical composition, a food supplement or a medical food. In one embodiment, the stabilized ACC or the composition is administered via a systemic administration. For example, the composition is administered orally, sublingually or rectally. Alternatively the composition is administered intravenously, intradermally, intramuscularly, intraperitoneally, subcutaneously, ocularly, sublingually, intranasally, by inhalation, intraspinally, intracerebrally, and transdermally. In one embodiment, the composition is administered orally. According to one embodiment, the method comprises administering a pharmaceutical composition comprising stable ACC as described above.

According to another aspect, the present invention provides amorphous calcium carbonate stabilized by at least one stabilizer for preparing a medicament for use in treating a leukemia. According to one embodiment, the leukemia is a chronic leukemia such as chronic lymphocytic leukemia, chronic myelogenous leukemia, and Hairy cell leukemia or an acute leukemia such as acute myeloid leukemia and acute lymphoblastic leukemia. According to one particular embodiment, the leukemia is CLL. According to one embodiment, the treating comprises treating at the early stages of the disease e.g. at stage 0. According to a further embodiment, the method comprises administering about 500 mg/day to about 5000 mg/day, about 750 mg/day to about 4000 mg/day of ACC, about 1000 mg/day to about 3000 mg/day, or about 1500 mg/day to about 2500 mg/day of stabilized ACC. According to some embodiments, the stabilizing agent is selected from the group consisting of a polyphosphate such as triphosphate, pyrophosphate, and hexametaphosphate; phosphorylated amino acid such as phosphoserine or phosphothreonine, bisphosphonate such as alendronate, etidronic acid, zoledronic acid and medronic acid; organic acid such as citric acid and tartaric acid; and any combination thereof.

The terms "comprising", "comprise(s)", "include(s)", "having", "has", and "contain(s)" are used herein interchangeably and have the meaning of "consisting at least in part of". When interpreting each statement in this specification that includes the term "comprising", features other than that or those prefaced by the term may also be present. Related terms such as "comprise" and "comprises" are to be interpreted in the same manner The terms "have", "has", having" and "comprising" may also encompass the meaning of "consisting of" and "consisting essentially of", and may be substituted by these terms. The term "consisting of" excludes any component, step or procedure not specifically delineated or listed. The term "consisting essentially of" means that the composition or component may include additional ingredients, but only if the additional ingredients do not materially alter the basic and novel characteristics of the claimed compositions or methods.

As used herein, the term "about", when referring to a measurable value such as an amount, a temporal duration, and the like, is meant to encompass variations of +/−10%, or +/−5%, +/−1%, or even +/−0.1% from the specified value.

The term "or" as used herein, denotes alternatives that may, where appropriate, be combined; that is, the term "or" includes each listed alternative separately as well as their combination if the combination is not mutually exclusive.

Having now generally described the invention, the same will be more readily understood through reference to the following examples, which are provided by way of illustration and are not intended to be limiting of the present invention.

EXAMPLES

A 72 years old man, generally healthy, showed a graduate increase in leucocytes values in several consequent blood tests. In addition, "basket cells" were observed and the person showed a reduction in the vitality; the man tended to fall asleep frequently.

No other symptoms that may be attributed to chronic lymphocytic leukemia (CLL) were observed. The person was diagnosed as stage 0 CLL patient and started a treatment with amorphous calcium carbonate (ACC) at Nov. 20, 2015 (five days after the blood test) according to the following regiment:

During the first three weeks: 3 Density® tablets/day orally (Density® to Amorphical Ltd.).

After three weeks, the daily dose was elevated to 6 Density® tablets/day.

Each Density® tablet contains 666 mg ACC as API (i.e. Amorphous CaCO3+Aerosil+drug substance stabilizers) which corresponds to 500 mg CaCO3, and equivalent to 200 mg elemental calcium (hereinafter the dose refers to the amount of elemental calcium).

The results of several consecutive blood tests (before and after the beginning of ACC administration) are presented in Tables 1 and 2.

TABLE 1

Full blood count values in several consecutive blood test

| test | 25/3/15 | 20/8/2015 | 15/11/15 | 7/12/15* | 17/2/16* | Normal range |
|---|---|---|---|---|---|---|
| WBC (leucocytes) | 25.9 | 38.8 | 52.1 | 55.4 | 50.3 | 4.5-11 |
| RBC | | 4.73 | 4.91 | 5.24 | 4.59 | 4.5-5.5 |
| hemoglobin | | 15 | 15.4 | 16.1 | 14.4 | 13.5-18 |
| hematocrit | | 43.4 | 46.2 | 49.3 | 43.6 | 41-53% |
| MCV | | 92 | 94 | 94 | 95 | 79-97 |
| MCH | | 31.7 | 31.4 | 30.7 | 31.4 | 27-34 |
| MCHC | | 34.6 | 33.3 | 32.7 | 33 | 32-36 |
| RDW | | 13.4 | 14.1 | 14.2 | 14.1 | 11.6-15 |
| platelets | 146 | 139 | 144 | 149 | 141 | 150-450 |
| MPV- | | 12.5 | 13 | 12.4 | 11.9 | 8.5-12.9 |
| Neutrophils % confirm | 9.8 | 19 | 6 | 13 | 18 | 40-75 |
| Lymphocytes % confirm | 83.1 | 72 | 91 | 84 | 77 | 22-44 |
| Monocytes % confirm | | 8 | 2 | 3 | 4 | 3-13 |
| eosinophils | | 1 | 0 | 0 | 1 | 0-6 |
| basophils | | 0 | 1 | 0 | 0 | 0-2 |
| presence of basket cells | X | X | X | X | X | 0 |
| PH(u) | | — | — | — | 6.5 | 5-8 |
| nitrite | | — | — | — | — | |
| ketone | | — | — | — | — | |
| glucose | | — | — | — | — | |

TABLE 1-continued

Full blood count values in several consecutive blood test

| test | 25/3/15 | 20/8/2015 | 15/11/15 | 7/12/15* | 17/2/16* | Normal range |
|---|---|---|---|---|---|---|
| urobilinogen | — | — | — | — | | |
| protein | — | — | — | — | | |
| leucocytes | — | — | — | — | | |
| erythrocytes | — | — | — | 10 | | 0-10 |
| Immunoglobulin M | 32.7 | 34.7 | 38.3 | 30.5 | | 40-230 mg/dl |
| Immunoglobulin G | 731.9 | 817.5 | 832.5 | 775.8 | | 737-1607 mg/dl |
| Immunoglobulin A | 199.8 | 210.7 | 209.8 | 199.9 | | 80-520 mg/dl |

RBC—red blood cells;
MCV—mean cell volume;
MCHC—M.cell HB count;
RDW—red cell distri.width;
MPV—mean platelet volume.
*the were tests performed after the beginning of ACC administration

TABLE 2

The WBC count in several consecutive tests

| | February 2013 | June 2014 | July 2014 | March 2015 | August 2015 | 15 Nov 2015 | *December 2015 | *February 2016 | Normal range |
|---|---|---|---|---|---|---|---|---|---|
| WBC | 13.8 | 25 | 22.7 | 25.9 | 38.8 | 52.1 | 55.4 | 50.3 | 4.5-11 |
| % Lymphocytes | | | | 83.1 | 72.6 | 96 | 84 | 77 | 22-44 |
| % Monocytes | 3 | 4 | | | 8 | 2 | 3 | 4 | 3-13 |
| % Neutrophils | | | | 9.8 | 19 | 6 | 13 | 18 | 40-75 |

*the tests were performed after the beginning of ACC administration.

It can be clearly seen that the elevation in WBC count was stopped after the patient started administrating ACC, and actually, the WBC count was reduced in the last blood test. In addition, an improvement in several other parameters, e.g. an increase in myocytes and neutrophils count was observed. Moreover, the patient became much more vital; the person did no longer tend to fall asleep as frequently as before the treatment.

As follows from these results, administration of ACC allows preserving a substantially constant level of WBC indicating that the treatment effectively prevents further progression of CLL and maintains it at zero level.

Although the present invention has been described herein above by way of preferred embodiments thereof, it can be modified, without departing from the spirit and nature of the subject invention as defined in the appended claims.

The invention claimed is:

1. A method of treating a chronic lymphocytic leukemia (CLL) at early stage of the disease in a subject in need thereof comprising administering a composition comprising an effective amount of amorphous calcium carbonate (ACC) stabilized by at least one stabilizing agent.

2. The method of claim 1, wherein the early stage is a watchful waiting stage.

3. The method of claim 1, wherein the early stage is stage 0 or at stage I of the disease.

4. The method of claim 1, wherein the stabilizer is selected from the group consisting of polyphosphate, organic acid, phosphorylated amino acids, bisphosphonate, phosphorylated organic acid, phosphoric or sulfuric ester of hydroxy carboxylic acid, hydroxyl bearing organic compound combined with alkali hydroxides and any combination thereof.

5. The method of claim 4, wherein the polyphosphate is an inorganic polyphosphate selected from triphosphate, pyrophosphate and hexametaphosphate; the phosphorylated amino acid is selected from phosphoserine or phosphothreonine; the organic acid is selected from citric acid and tartaric acid; and the bisphosphonate is selected from alendronate, etidronic acid, zoledronic acid and medronic acid.

6. The method of claim 5, wherein the stabilizing agent is a polyphosphate or bisphosphonate and the molar ratio between P atoms of the stabilizing agent and Ca atoms of the ACC is about 1:90 to 1:1.

7. The method of claim 1, wherein treating a chronic lymphocytic leukemia (CLL) at early stage of the disease comprises at least one of the group consisting of ceasing, retarding, reversing or preventing the development of the leukemia.

8. The method of claim 7, wherein ceasing, retarding, reversing or preventing the development of the chronic lymphocytic leukemia (CLL) at early stage of the disease comprises ceasing, retarding or reversing the progression of lymphocytosis.

9. The method of claim 8, wherein ceasing the progression of lymphocytosis comprises preserving the level of white blood cells at the same level for at least 3 months.

10. The method of claim 1, comprising administering about 500 mg/day to about 5000 mg/day of ACC.

11. The method of claim 1, wherein the composition comprising ACC and at least one stabilizer is formulated as a pharmaceutical composition or nutraceutical composition, a food supplement or a medical food.

* * * * *